US006677169B1

(12) United States Patent
Li

(10) Patent No.: US 6,677,169 B1
(45) Date of Patent: Jan. 13, 2004

(54) METHOD AND SYSTEM FOR BACKSIDE DEVICE ANALYSIS ON A BALL GRID ARRAY PACKAGE

(75) Inventor: Xia Li, Fremont, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 231 days.

(21) Appl. No.: 09/922,417

(22) Filed: Aug. 2, 2001

(51) Int. Cl.[7] .............................................. H01L 21/66
(52) U.S. Cl. .............................. 438/15; 438/14; 438/16
(58) Field of Search ............................... 438/15, 16, 14

(56) References Cited

U.S. PATENT DOCUMENTS

| 5,216,278 A | * | 6/1993 | Lin et al. ................... 257/688 |
| 5,821,549 A | * | 10/1998 | Talbot et al. ............... 250/307 |
| 6,245,586 B1 | * | 6/2001 | Colvin ........................ 438/15 |
| 6,395,580 B1 | * | 5/2002 | Tseng ......................... 438/108 |

\* cited by examiner

Primary Examiner—Amir Zarabian
Assistant Examiner—Jeff Vockrodt
(74) Attorney, Agent, or Firm—Winstead Sechrest & Minick P.C.

(57) ABSTRACT

A method and system for preparing a device for analysis is disclosed. In the present invention, the device to be prepared includes a semiconductor die coupled to a first surface of a package substrate. The first surface of the package substrate includes an interconnect pattern for electrically coupling the semiconductor die to a plurality of solder ball connectors disposed on a second surface of the package substrate. The method and system for preparing the device for backside analysis comprises removing the plurality of solder ball connectors, exposing the interconnect pattern, and then exposing a backside of the semiconductor die. The method further includes preparing the backside of the semiconductor die for diagnostic testing. Electrical contact with the semiconductor die is established via the exposed interconnect pattern.

12 Claims, 5 Drawing Sheets

METHOD AND SYSTEM FOR BACKSIDE DEVICE ANALYSIS ON A BALL GRID ARRAY PACKAGE

FIELD OF THE INVENTION

The present invention relates to integrated circuit device analysis, and more particularly to backside device analysis on ball grid array devices using a planar backside chip thinning system.

BACKGROUND OF THE INVENTION

With advancements in integrated circuit technology, electronic devices have become much more powerful and have shrunken in size. Devices that once occupied an entire desk top now fit into a jacket pocket. The drive toward smaller and portable electronic products has pushed the development of chip scale packages (CSPs). CSPs incorporate semiconductor devices into a compact configuration by accommodating leads connected to a circuit forming surface of a semiconductor chip within a size of the chip. For instance, CSPs are typically in the range of 1.2 times the size of the semiconductor die. Comparing the size of an 8 Mb flash memory device, such as a TSOP48 (Thin Small Outline Package), which is approximately 18.4 mm×12 mm, the size of a CSP, such as a fine pitch ball grid array (FBGA), is approximately 6 mm×9 mm.

A typical CSP is a ball grid array, which is a surface mount chip package that uses a grid of solder balls to couple the integrated circuit device to a planar, such as a circuit board. One type of ball grid array (BGA) is the fine pitch BGA (FBGA), which can incorporate a polyimide (PI) tape package substrate (FBGA-PI) or a bismaleimide triazine (BT) package substrate (FBGA-BT). FIGS. 1 and 2 illustrate partial cross-sectional diagrams of typical FBGA devices. FIG. 1 illustrates a single die package 10, such as an AM29LV160DT manufactured by Advanced Micro Devices, Inc. of Sunnyvale, Calif., while FIG. 2 illustrates a stacking two dice package 50, known as a multi-chip package (MCP). Both packages are commonly used for memory integrated circuit devices, and the MCP is widely used for high density and mixed type memory integrated devices.

As is shown in FIG. 1, an FBGA package 10 includes an integrated circuit die 12 coupled to a package substrate 14. Electrical connections for the die 12 are provided by gold bond wires 16, which connect a plurality of bond pads 18 on the die 12 to an interconnect pattern 20 on the package substrate 14. The interconnect pattern 20 provides an electrical path (not shown) from the bond pads 18 on the die 12 to a plurality of solder ball connectors 22, which attach the package 10 to a planar (not shown). The die 12 and bond wires 16 are encapsulated by a molding compound 24. A solder mask layer 26 defines the location of each solder ball 22.

The MCP 50, shown in FIG. 2, is substantially similar in structure to the single die package 10, except that a first die 51 is stacked on a second die 52, which in turn is coupled to the package substrate 14'. A plurality of bond wires 16' couple a plurality of bond pads 18', 18" on the first die 51 and the second die 52 to the interconnect pattern 20', which provides an electrical path (not shown) to a plurality of solder ball connectors 22'.

As stated above, FBGA packages such as those illustrated in FIGS. 1 and 2 are gaining widespread use in portable electronic devices. As with all integrated circuits, testing and fault isolation analysis is essential to improving the design and performance of the semiconductor device. Conventional analysis techniques involve accessing the integrated circuit from the front, or top, side. Nevertheless, frontside analysis has become more difficult as integrated circuits have become more complex. For instance, integrated circuits are distributed and interconnected over multiple layers, and oftentimes, the active regions of the integrated circuit are buried beneath metal buses, which obscure or prevent analysis from the frontside. Access to those active regions would require destroying the upper metal layers, thereby destroying the integrated circuit. Moreover, frontside analysis is not feasible for certain CSPs, such as flip chips (e.g., micro BGAs) and MCPs incorporating stacked dice.

In response, techniques have been developed to analyze an integrated circuit from the backside, i.e. the bottom, of the semiconductor die. The sample is prepared by using a planar backside chip thinning system, such as the Chip Un-Zip ™ system manufactured by Hypervision, Inc. of Fremont, Calif., to remove any backside mold compound and to expose the backside of the semiconductor die. The backside surface of the die can be polished to facilitate backside imaging if such analysis is required. In this manner, access to the active regions in the integrated circuit is possible because the upper layers, including the metal buses, are no longer obscuring the active regions. Circuit fault isolation analysis, such as emission microscope analysis, can be performed without destroying the integrated circuit.

While backside analysis provides a reasonable alternative for most integrated circuit packages, it is not feasible for BGA packages. FIG. 1A illustrates the FBGA package of FIG. 1 after conventional preparation for backside analysis. As noted above, the BGA package is connected electrically to the planar through the solder ball connectors located on the backside of the package. The backside of the die cannot be exposed for backside analysis without removing the solder ball connectors, without which, the BGA package would be electrically isolated. Thus, conventional sample preparation for backside analysis would impair electrical connectivity at the package level, i.e. electrical connection between the package and the planar. Such electrical connectivity is required for circuit fault isolation analysis, such as emission microscope analysis.

Accordingly, a need exists for a system and method for preparing a BGA device for backside analysis. The present invention addresses such a need.

SUMMARY OF THE INVENTION

A method and system for preparing a device for diagnostic analysis is disclosed. The device to be prepared includes a semiconductor die coupled to a first surface of a package substrate, which includes an interconnect pattern for electrically coupling the die to the package substrate. The package substrate includes a plurality of solder ball connectors that are electrically connected to the interconnect pattern and are disposed on a second surface of the package substrate. The method and system for preparing the device for backside analysis comprises removing the plurality of solder ball connectors, selectively removing a first portion of the second surface of the package substrate to expose the interconnect pattern, and then selectively removing a second portion of the package substrate to expose a backside of the semiconductor die. The method further includes preparing the backside of the semiconductor die for diagnostic testing. Electrical contact with the semiconductor die is established via the exposed interconnect pattern.

Through the aspects of the present invention, backside analysis of a device which utilizes solder ball connectors, can be performed while maintaining electrical connectivity with the device. Instead of relying on the solder ball connectors, the present invention establishes electrical connectivity with the device through the interconnect pattern on the package substrate. Accordingly, the integrated circuits can be powered to perform fault isolation analysis.

DETAILED DESCRIPTION

The present invention relates to integrated circuit device analysis, and more particularly to backside device analysis on a ball grid array package. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Figure 1:
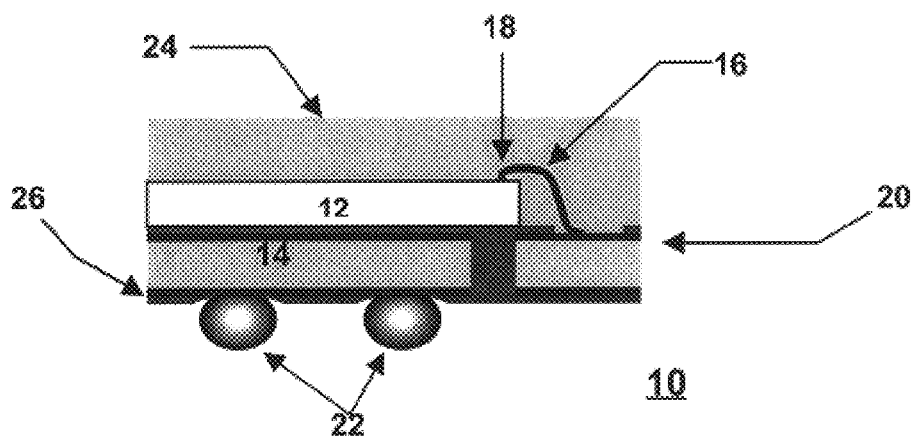
FIG. 1 illustrates a single die ball grid array (BGA) package.
Figure 1A:
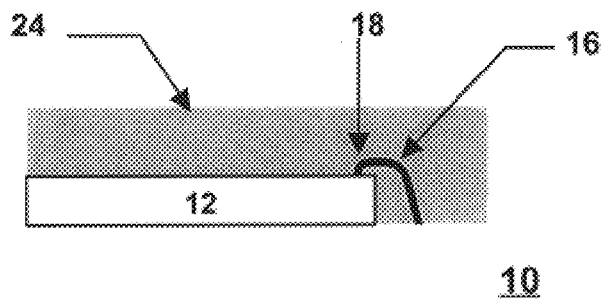
FIG. 1A illustrates the BGA package after conventional sample preparation for backside analysis.
Figure 2:
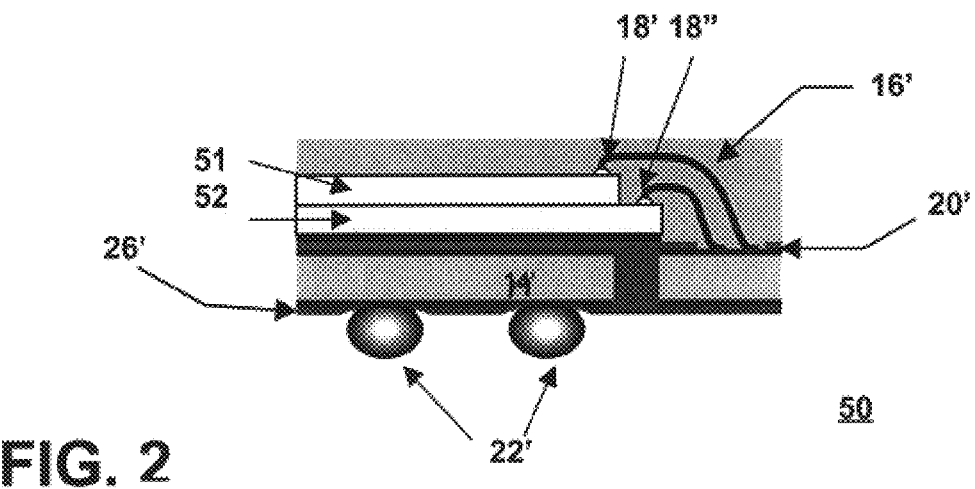
FIG. 2 illustrates a multi-chip BGA package.

Traditional backside sample preparation techniques require removing the entire backside of the sample to access the backside of the semiconductor die. Removing the entire backside of a BGA package to expose the backside of the semiconductor die, however, presents problems. By removing all the material between the backside of the BGA package and the semiconductor die, e.g., the solder ball connectors, and the package substrate, the BGA package becomes electrically isolated, i.e., electrical connectivity at the package level is destroyed. (See FIG. 1A). Therefore, backside analysis, such as circuit fault isolation analysis, cannot be performed because power cannot be supplied to the die.

The present invention provides a method and system for preparing a BGA package for backside analysis, such that electrical connectivity to the package is maintained despite removing the solder ball connectors. In a preferred embodiment of the present invention, the package substrate is selectively removed in order to expose, in one region, the interconnect pattern, and in another region, the backside of the semiconductor die. As stated above, the die in a BGA package is electrically coupled to the package via the interconnect pattern, which in turn is electrically connected to the solder ball connectors. Thus, even if the solder ball connectors are removed, the die can be powered through the interconnect pattern.

Figure 3:
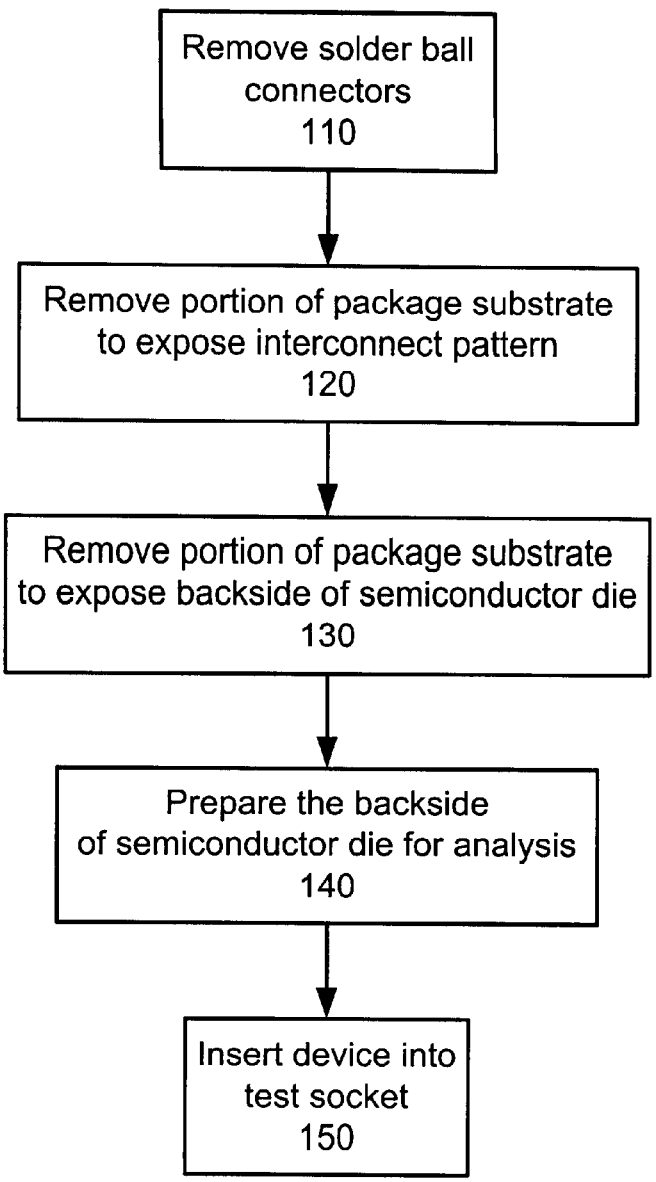
FIG. 3 is a flow chart illustrating a method in accordance with a preferred embodiment of the present invention.
Figure 4A:
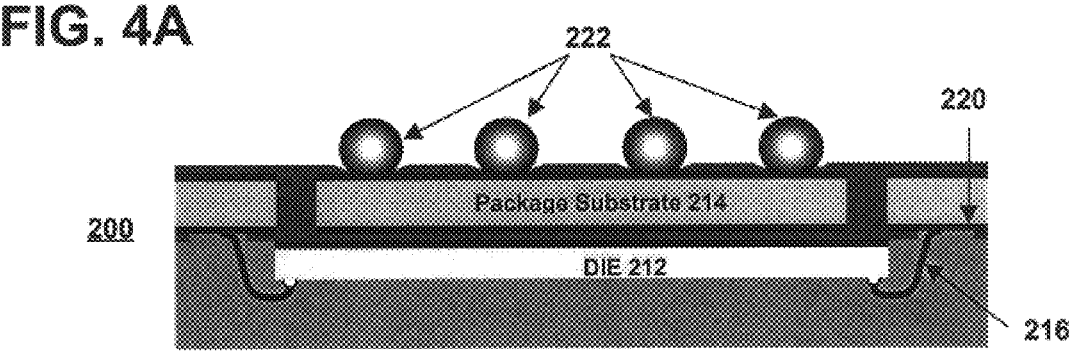
FIGS. 4A–4E illustrate a single die BGA during preparation for backside analysis in accordance with a preferred embodiment of the present invention.
Figure 4B:
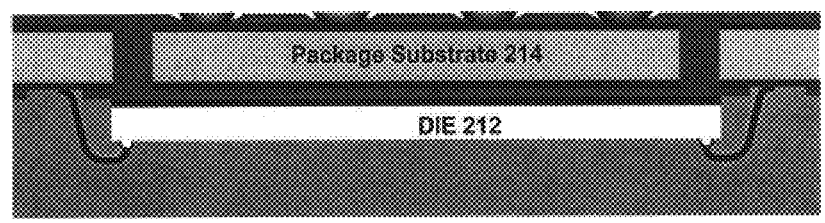

To further describe the method in accordance with the present invention, please refer to FIG. 3 and the accompanying illustrations in FIGS. 4A–4E. FIG. 3 is a flowchart of the method in accordance with the present invention. FIG. 4A illustrates a cross-sectional view of the FBGA package 200 to be prepared for backside analysis. The process starts by removing the solder ball connectors 222 via step 1 10. The solder ball connectors 222 can be removed by any appropriate means, such as by using parallel mechanical polishing techniques, which are well known to those skilled in the art. The resultant structure is illustrated in FIG. 4B. At this stage, the die 212 is electrically isolated because the solder ball connectors 222 have been removed.

Figure 4C:
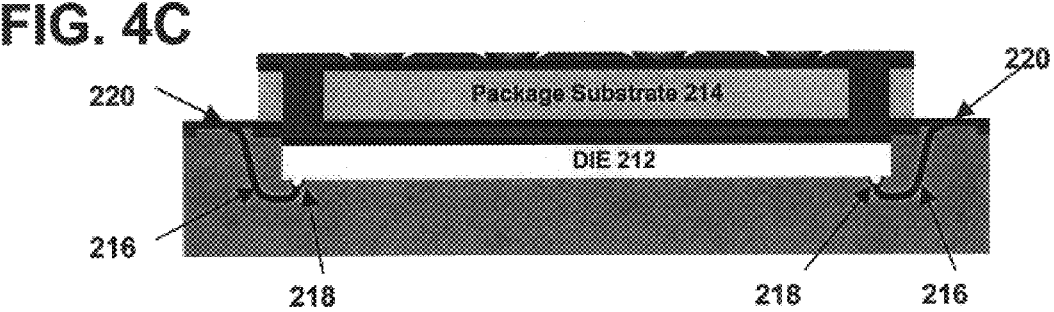

In step 120, however, electrical connectivity is restored. In step 120, a portion of the package substrate 214 adjacent to the interconnect pattern 220 is removed, exposing the interconnect pattern 220. As is shown in FIG. 4C, the interconnect pattern 220 is located on both sides of the semiconductor die 212, and both interconnect patterns 220 are exposed (via the backside) after the removal of the package substrate 214. At this point, because the bond wires 216 electrically couple the interconnect pattern 220 to the bond pads 218 on the die 212, electrical connectivity with the die 212 is restored via the interconnect pattern 220.

Figure 4D:

Next, in step 130, another portion of the package substrate 214 adjacent to the die 212 is selectively removed, exposing the backside of the die 212. FIG. 4D illustrates the FBGA package after removing this portion of the package substrate 214. Because only the portion of the package substrate 214 adjacent to the die 212 is removed, the interconnect pattern 220 remains intact and exposed.

Although the above description indicates exposing the interconnect pattern 220 before exposing the backside of the die 212, one of ordinary skill in the art would appreciate that exposing the die 212 before exposing the interconnect pattern 220 would also serve the same purpose. Removal of the package substrate 214 (and other materials, e.g., solder mask) is preferably accomplished using a planar backside chip thinning system, such as a Chip Un-Zip™ system manufacture by Hypervision, Inc. of Fremont, Calif. Such a tool is a semi-automated high-speed diamond cutting tool. The tool can readily strip encapsulation materials, as well as package substrates and solder masking. Moreover, the Chip Un-Zip tool is capable of high precision milling for thinning a substrate and/or polishing a surface.

Figure 4E:

Referring again to FIG. 3, the semiconductor die 212 is now ready to be prepared for backside analysis in step 140. For example, for circuit fault isolation analysis, such as photon emission analysis, the die 212 must be thinned to observe the photon emissions generated by a circuit fault. Moreover, the die's 212 surface must be polished to minimize surface defects which can cause scattering. The Chip Un-Zip tool is preferably used to thin and polish the backside of the die 212. FIG. 4E illustrates the FBGA package after the die 212 has been exposed, thinned, and polished. Again, the preparing step 140 is limited to the die 212, and therefore, the interconnect pattern 220 remains intact and exposed.

Figure 5A:
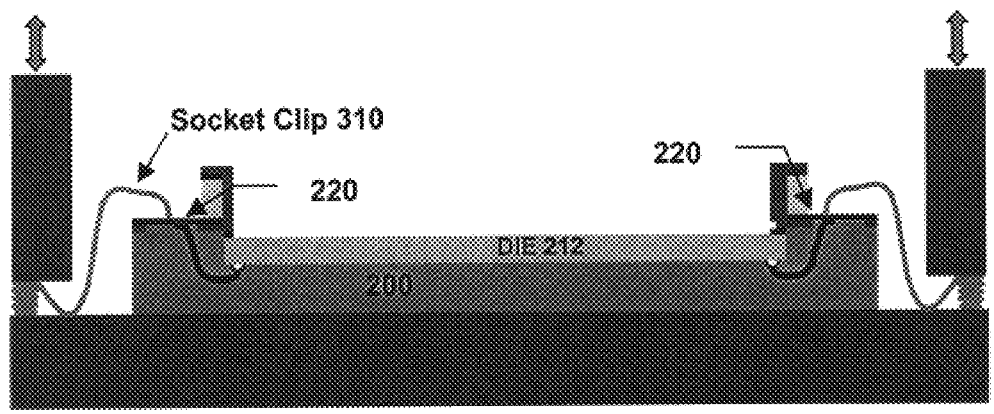
FIGS. 5A and 5B illustrate a test socket that can be used in accordance with the present invention.
Figure 5B:
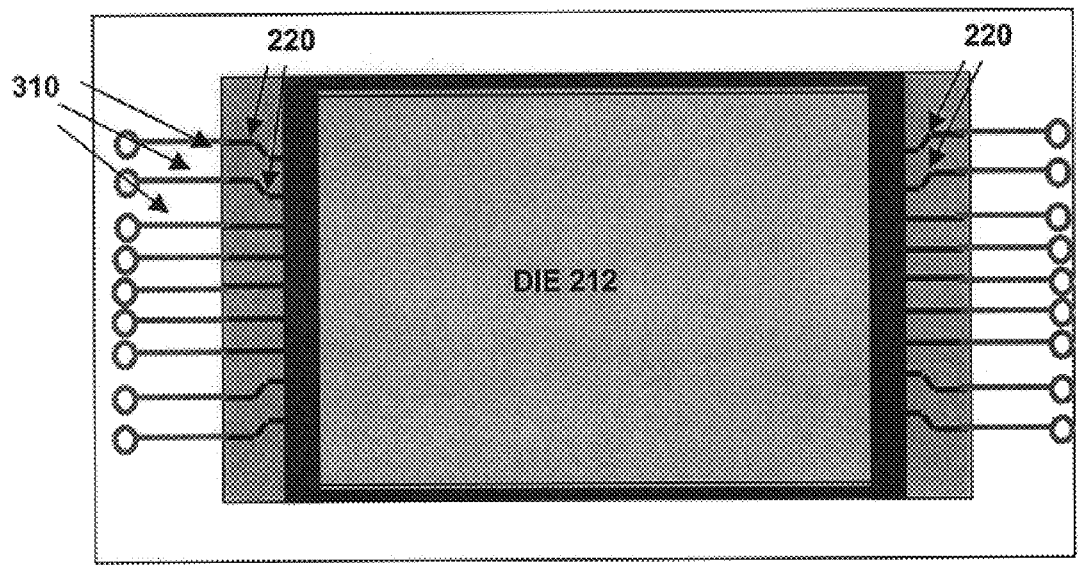

In step 150, the prepared FBGA package 200 is placed into a test socket 300, such as that illustrated in FIG. 5. As is shown, the test socket 300 includes a plurality of clips 310 that make electrical contact with the interconnect pattern 220 on both sides of the die 212. In this manner, the FBGA sample 200 is ready for backside testing and diagnostic analysis, such as photon emission analysis.

Through aspects of the present invention, backside analysis of a package that utilizes solder ball connectors to provide electrical connectivity at the package level, can be performed while maintaining electrical connectivity with the device. Instead of relying on the solder ball connectors, the present invention establishes electrical connectivity with the device through the interconnect pattern on the package substrate. Accordingly, the die can be powered and fault isolation testing, such as photon emission analysis, can be performed.

Although the present invention has been described in accordance with the embodiments shown, one of ordinary skill in the art will readily recognize that there could be variations to the embodiments and those variations would be within the spirit and scope of the present invention. For instance, while a single die FBGA has been used to illustrate the present invention, the present invention is not limited to such BGA packages. In addition, alternative material removal techniques, besides the planar chip thinning technique described, could be utilized to accomplish the present invention. Accordingly, many modifications may be made by one of ordinary skill in the art without departing from the spirit and scope of the appended claims.

What is claimed is:

1. A method for preparing a device for analysis, the device including a semiconductor die coupled to a first surface of a package substrate, the first surface of the package substrate having an interconnect pattern for electrically coupling the semiconductor die to a plurality of solder ball connectors disposed on a second surface of the package substrate, the method comprising the steps of:

a) removing the plurality of solder ball connectors;
   b) exposing the interconnect pattern by selectively removing a first portion of the package substrate;
   c) exposing a backside of the semiconductor die by selectively removing a second portion of the package substrate; and
   d) preparing the backside of the semiconductor die for diagnostic testing, wherein electrical connectivity with the semiconductor die is established via the exposed interconnect pattern.

2. The method of claim 1, wherein the semiconductor die includes a plurality of bond pads, the plurality of bonds being electrically coupled to the interconnect pattern via a plurality of bond wires.

3. The method of claim 1, wherein the step (a) of removing the plurality of solder ball connectors further includes:

a1) stripping the plurality of solder balls using parallel mechanical polishing.

4. The method of claim 1, wherein a solder mask is deposited on the second surface of the package substrate for patterning the plurality of solder ball connectors.

5. The method of claim 1, wherein step (c) of selectively removing the second portion of the substrate includes:

c1) providing a high-speed diamond cutting tool;
   c2) removing the solder mask layer over the second portion of the package substrate using the high-speed diamond cutting tool; and
   c3) removing the second portion of the package substrate using the high-speed diamond cutting cool.

6. The method of claim 1, wherein the step (d) of preparing the backside of the semiconductor die further includes:

d1) thinning the backside of the semiconductor die; and
   d2) polishing the backside of the semiconductor die.

7. The method of claim 1, wherein the device is a ball grid array.

8. A method for analysis of a ball grid array (BGA) device, the BGA device including a semiconductor die coupled to a fist surface of a package substrate, the first surface of the package substrate having an interconnect pattern for electrically coupling the semiconductor die to a plurality of solder ball connectors disposed on a second surface of the package substrate, the method comprising the steps of:

a) removing the plurality of solder ball connectors;
   b) selectively removing a first portion of the package substrate to expose the interconnect pattern;
   c) selectively removing a second portion of the package substrate to expose a backside of the semiconductor die;
   d) preparing the backside of the semiconductor die for diagnostic testing; and
   e) inserting the BGA device into a test socket, whereby electrical contact between the semiconductor die and the test socket is established via the exposed interconnect pattern.

9. The method of claim 8, wherein the backside analysis comprises photon emission analysis.

10. The method of claim 9, wherein step (d) of preparing the backside of the semiconductor die includes:

d1) thinning the backside of the semiconductor die; and
    d2) polishing The backside of the semiconductor die.

11. The method of claim 8, wherein a high precision milling system is used for steps (b)–(d).

12. The method of claim 8, wherein the test socket includes a plurality of clips, and the plurality of clips contact the exposed interconnect pattern when the BGA device is inserted into the test socket, thereby establishing an electrical connection between the semiconductor die and the test socket.

* * * * *

UNITED STATES PATENT AND TRADEMARK OFFICE
CERTIFICATE OF CORRECTION

PATENT NO.      : 6,677,169 B1
DATED           : January 13, 2004
INVENTOR(S)     : Xia Li It is certified that error appears in the above-identified patent and that said Letters Patent is hereby corrected as shown below:

Column 5,
Line 49, before "substrate" please insert -- package --.

Column 6,
Line 39, please replace "The" with -- the --.

Signed and Sealed this

Twenty-fifth Day of May, 2004

JON W. DUDAS
*Acting Director of the United States Patent and Trademark Office*